United States Patent [19]
Pifferi

[11] 3,984,461
[45] Oct. 5, 1976

[54] 3-0-(BETA-CARBOBENZYLOXYPROPIONYL)-11-OXO-18-BETA-OLEAN-12-EN-30-OIC ACID

[75] Inventor: Giorgio Pifferi, Milan, Italy

[73] Assignee: I.S.F. S.p.A., Milan, Italy

[22] Filed: Jan. 25, 1972

[21] Appl. No.: 220,695

[30] Foreign Application Priority Data
Aug. 6, 1971  Italy................................. 27287/71

[52] U.S. Cl. ......................... 260/485 L; 260/485 H
[51] Int. Cl.² ......................................... C07C 69/40
[58] Field of Search ..................... 260/485 L, 468.5

[56] References Cited
FOREIGN PATENTS OR APPLICATIONS
843,133  8/1960  United Kingdom OTHER PUBLICATIONS
Technique of Organic Chemistry, vol. II, Interscience Publishers, Inc., N.Y., pp. 123–124 (1956).

Primary Examiner—Jane S. Myers
Attorney, Agent, or Firm—Shlesinger, Fitzsimmons & Shlesinger

[57] ABSTRACT

A two-step method for the preparation of 3-0-(beta-carboxypropionyl-18-beta-glycyrrhetic acid (carbenoxolone) is disclosed, which comprises the steps of condensing beta-glycyrrhetic acid with anhydrous beta-carbobenzyloxypropionic acid (or a derivative thereof such as its chloride or anhydride), the result being 3-O-(beta-carbobenzyloxypropionyl)-11-oxo-18-beta-olean-12-en-30-oic acid, the latter compound being then debenzylated with hydrogen under normal temperature and pressure conditions, in an alcoholic solvent (alcohols having from $C_1$ to $C_5$) and in the presence of catalytic amounts of a noble metal (e.g. palladium), thus obtaining the expected compound.

1 Claim, No Drawings

3-O-(BETA-CARBOBENZYLOXYPROPIONYL)-11-OXO-18-BETA-OLEAN-12-EN-30-OIC ACID

This invention relates to a novel method for the preparation of derivatives of the beta-glycyrrhetic acid, more particularly for the preparation of the 3-O-(beta-carboxypropionyl)-18-beta glycyrrhetic acid (carbenoxolone) having the formula:

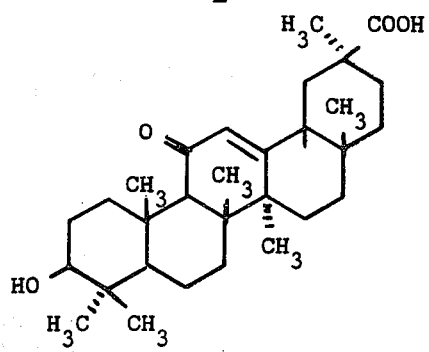

(I)

and of the salts thereof with physiologically acceptable cations.

The invention also relates to the preparation of an important intermediate, that is, the 3-O-(beta-carbobenzyloxypropionyl)-11-oxo-18-beta-olean-12-en-30-oic acid having the formula:

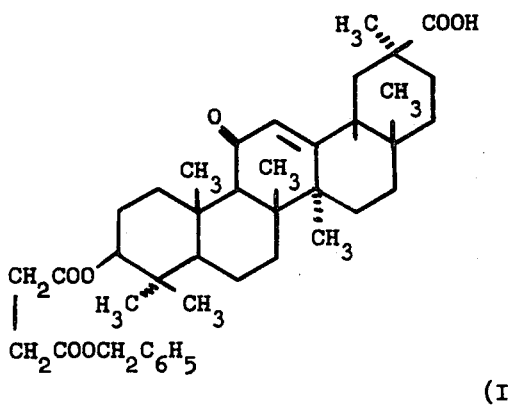

(II)

It is known that the beta-glycyrrhetic acid, having the formula:

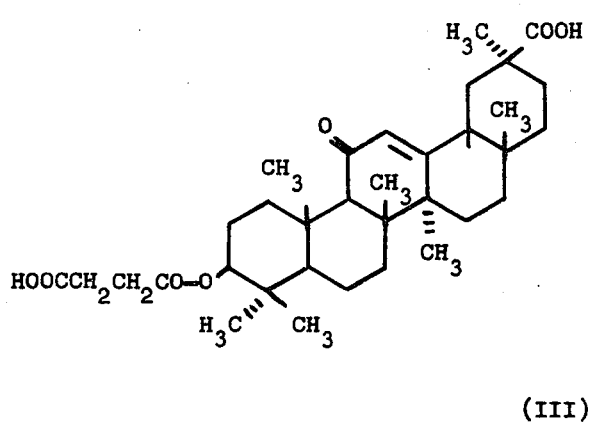

(III)

is derived from a glycoside of natural origin and a few derivatives thereof, among which, more particularly, the succinic half-ester (III) has interesting pharmacological properties possessing considerable therapeutical utility (anti-inflammatory and anti-ulcer action). The methods as claimed hitherto for the preparation of (III) suggest the acylation of the beta-glycyrrhetic acid according to conventional methods, by reacting either succinic acid or its anhydride with (I), preferably in pyridine, at high temperatures and for a long period of time (S. Gottfried and L. Baxendale, British Pat. No. 843,133).

Under such drastic conditions, it is noted that the reaction takes place with a considerable darkening and formation of foreign substances, that the yields are not satisfactory, and the end product, having a cream yellow colour, does not exhibit the most desirable analytical specifications which can be attributed to a pure product. On account of the complicated molecular structure of the beta-glycyrrhetic acid and its numerous centres of asymmetry, it is deemed that the above mentioned drastic conditions are not the most suitable for its succinylation. As a matter of fact, the technical literature reports a number of isomerizations that the glycyrrhetic acid and its derivatives undergo as a result of an alkaline or acidic treatment, the consequence being a final inversion of the configuration, more particularly at the centre of asymmetry at $C_{18}$ (J. M. Beaton and F. S. Spring, J. Chem. Soc., 3126 (1955); F. Lauria, Germ. Pat. No. 1,073,491). Thus also, the hexa-atomic nucleus A of (I) can be rearranged in a dehydrating environment to a penta-atomic nucleus due to elimination of water (V. Askam, C. M. Barnes and H. J. Smith, J. Pharm. Pharmac., 18, 168 (1966)) and the carboxylic group at $C_{20}$ can be lactonized in an oxidising milieu (J. Simonsen and W. C. J. Ross "The Terpenes", Cambridge University Press, 1957, Vol. V, page 462). It is apparent that these and other structural degradations are encouraged by the above mentioned conditions of succinylation and impair the yields and the quality of the end product.

The method according to the present invention does away with the drawbacks enumerated above and permits carrying out the hemisuccinylation of the beta-glycyrrhetic acid (I) according to a novel procedure which adopts particularly mild or bland conditions of reaction and the use of a novel succinylating reagent. Consequently, both higher yields and a purer end product are obtained.

The method according to the present invention, as summarized by the following pattern:

(I) → (II) → (III)

thus comprises two stages, of which:

a. the first stage provides for the condensation of beta-glycyrrhetic acid (I) with anydrous beta-carbobenzyloxypropionic acid, the latter having the formula:

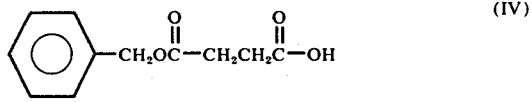
(IV)

or, as an alternative, with a more reactive derivative thereof, such as the chloride or the anhydride, having the formula:

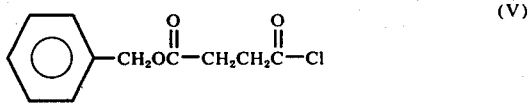
(V)

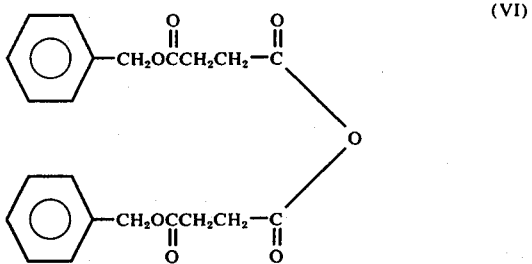
(VI)

respectively, the derivative (II) being thus obtained, that is, the 3-O-(beta-carbobenzyloxypropionyl)-11-oxo-18-beta-olean-12-en-30-oic acid, and b. the second stage provides for the debenzylation of the compound (II) with hydrogen, under normal pressure and temperature conditions, either in suspension or in solution in an alcoholic solvent selected from the group consisting of the alcohols having from 1 to 5 carbon atoms and in the presence of small amounts of a catalyst consisting of a noble metal in a finely divided state, carbenoxolone (III) being obtained with virtually theoretical yields.

It is important to emphasize that, as regards the first stage, when the condensation is carried out with the anhydride (VI), it takes place at temperatures below 100°C and in the presence of appropriate solvents, preferably aprotic solvents. When, conversely, the acid chloride (V) is used instead of the anhydride, the former, in turn, forms a new derivative as obtained by bland chlorination of the acid (IV) with thionyl chloride in the presence of anhydrous dimethylformamide. Possibly, it is also permissable to use, instead of the chloride, the corresponding bromide. The preparation and the use of the chloride (V) in the succinylation reactions are other original features of this invention. As a matter of fact, its use permits the esterification of the beta-glycyrrhetic acid (I) also at room temperature by avoiding any heating and operating in an aprotic solvent such as dioxane and in the presence of an appropriate tertiary organic base. The ester (II) possesses satisfactory characteristics of solubility in ethanol, from which it is readily purified by crystallization.

A further feature of the present method is represented by the production of the succinic half-ester (III) of the beta-glycyrrhetic acid by hydrogenolysis of the corresponding benzyl ester (II). The alkali metal salts of carbenoxolone can be prepared according to conventional methods of neutralization of (III) with an appropriate hydroxide, carbonate or bicarbonate of an alkali metal in an aqueous and/or alcoholic environment.

The particularly bland conditions required for performance of the novel method prevent the above enumerated shortcomings from occurring, that is, those of the conventional succinylation reagents, and significantly improve both the yields and the quality of the end product. As a matter of fact, carbenoxolone is obtained as a white microcrystalline solid (rather than "cream-coloured" as reported in the Brit. Pat. No. 843,133 cited above) with a melting point and $\delta_D^{20}$ in chloroform which are considerably higher. The purity of the end product (III) has a primary importance in the case of prolonged therapeutical treatments with carbenoxolone.

The invention will now be illustrated by a few exemplary embodiments to which there is no intention to limit the invention in any way.

EXAMPLE 1

Beta-carbobenzyloxypropionic acid chloride (V)

A solution of 5 grams of beta-carbobenzyloxypropionic acid (IV) in 50 ml. of thionyl chloride containing 0.5 ml of anhydrous dimethylformamide is allowed to stand, sheltered from moisture, for two days. The excess thionyl chloride is distilled off under a high vacuum, and the residue, which is a yellow oil, is heated in a flask to 110°C under an abs. pressure of 0.4 mmHg in order to strip the head fractions. The undistilled residue is taken up with ethyl ether, decolorized with charcoal, filtered and concentrated again. There are obtained about 3.48 grams (64% of theory) of (V) which is employed as such for the following stage.
Infrared spectrum: 1810 (C=O, acid chloride), 1750 (C=O ester), 1060 (C—O), 755 cm$^{-1}$ (phenyl)
Analysis : for $C_{11}H_{11}ClO_3$: Cl% = Calcd. 15.64; Found 16.05

EXAMPLE 2

Beta-carbobenzyloxypropionic acid anhydride (VI)

To 179 grams of beta-carbobenzyloxypropionic acid (IV) there are added 500 ml of acetic anhydride and the solution is heated on a boiling water bath for 45 minutes. The excess reactant is distilled off and the residue is crystallized from one liter of carbon tetrachloride, the result being 140 grams (81% of theory) of (VI), which has a melting point of 70°C–71°C.
Infrared spectrum (Nujol): 1820 (C=O anhydride), 1730 (C=O ester), 1090 (C—O), 738 cm$^{-1}$ (phenyl),

EXAMPLE 3

3-O-(beta-carbobenzyloxypropionyl)-11-oxo-18-beta-olean-12-en-30-oic acid (II).

Method A

A mixture of 4.7 grams of beta-glycyrrhetic acid (I) and 6 grams of beta-carbobenzyloxypropionic acid anhydride (VI) is heated in 17 ml anhydrous pyridine and heated to 80°C–90°C during one hour, then the mixture is allowed to cool at room temperaure and pured in cold, dilute sulphuric acid. The mass which has separated is extracted with chloroform, the extracts are washed with dilute $H_2SO_4$ and water, dried over $Na_2SO_4$ and evaporated. The residue is slurried with a small amount of ethyl ether, the solids are collected by filtration and crystallized from ethanol. 3-O-(beta-carbobenzyloxypropionyl)-11-oxo-18-beta-olean-12-en-30-oic acid (II) is obtained with a high yield as a white salt which melts at 213°C–216°C.

Infrared spectrum (Nujol): 3380 (OH carboxyl), 1740 (>C=O ester), 1720 (>C=O carboxyl), 1650 (>C=O conj. ketone), 740 cm$^{-1}$ (phenyl)

Analysis : for $C_{41}H_{56}O_7$ C% = Calcd. 74.50; H% = Calcd. 8.54; C% = Found 73.58; H% = Found 8.47

Method B

To a solution of 2.33 grams of beta-glycyrrhetic acid and 4.3 ml anhydrous pyridine in 23 ml of dioxane cooled at 10°C there is added dropwise with stirring a dioxane solution of 1.3 grams of beta-carbobenzyloxyprobionic acid chloride (V). Stirring is continued at room temperaure during 10 hours and the mixture is allowed to stand overnight. The solvent is distilled off in a vacuo and the residue is treated in the cold with diluted sulphuric acid. The residue is extracted with chloroform, the extracts are washed with dilute sulphuric acid and water, dried over sodium sulphate and evaporated. Isolation and purification of the product can be carried out under the same working conditions of method A above, the derivative (II) being obtained with high yields, virtually pure and identical.

EXAMPLE 4

3-O-(beta-carboxypropionyl)-18-beta-glycyrrhetic acid (III) (Carbenoxolone)

A solution in methanol of 2.5 grams of 3-O-(beta-carbobenzyloxypropionyl)-11-oxo-18-beta-olean-12-en-30oic acid (II) is hydrogenated with shaking with hydrogen at normal temperature and pressure in the presence of 0.45 grams of 10% palladium of charcoal as a catalyst. Once the absorption of a mole of hydrogen has been completed, the catalyst is filtered off cautiously and the alcoholic filtrate is concentrated to a volume of 10 ml approx. By prolonged cooling there is obtained, with virtually theoretical yields, the carbenoxolone (III) as a microcrystalline white solid having a melting point of 298°C–302°C.

Infrared spectrum (Nujol): 3480–2350 (OH carboxyl), 1750 (>C=O ester), 1720 (>C=O carboxyl), 1660 cm$^{-1}$ (>C=O conj. ketone).

$\alpha_D^{20} = +138°$ (C=1% in chloroform), $E_1{}_{cm}^{1\%} = 216$ at 250 millimicron in $CH_3OH$ Carboxyl percentage : 99.8% of theory.

What is claimed is:

1. 3-O-(beta-carbobenzyloxypropionyl)-11-oxo-18-beta-olean-12-en-30-oic acid having the formula:

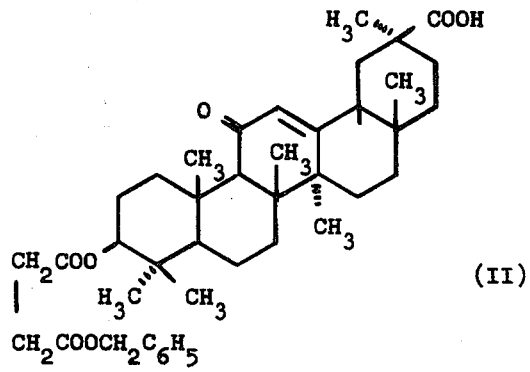

(II)

* * * * *